(12) United States Patent
Faccioli et al.

(10) Patent No.: US 10,828,162 B2
(45) Date of Patent: Nov. 10, 2020

(54) CORE FOR A SPACER

(71) Applicant: TECRES S.p.A., Sommacampagna (Verona) (IT)

(72) Inventors: Giovanni Faccioli, Monzambano (IT); Renzo Soffiatti, Nogara (IT)

(73) Assignee: TECRES S.P.A., Sommacampagna (IT)

( * ) Notice: Subject to any disclaimer, the term of this patent is extended or adjusted under 35 U.S.C. 154(b) by 0 days.

(21) Appl. No.: 16/066,412

(22) PCT Filed: Dec. 23, 2016

(86) PCT No.: PCT/IB2016/057964
§ 371 (c)(1),
(2) Date: Jun. 27, 2018

(87) PCT Pub. No.: WO2017/115249
PCT Pub. Date: Jul. 6, 2017

(65) Prior Publication Data
US 2019/0000630 A1    Jan. 3, 2019

(30) Foreign Application Priority Data
Dec. 30, 2015  (IT) .................. 102015000089320

(51) Int. Cl.
*A61F 2/30* (2006.01)
*A61F 2/36* (2006.01)

(52) U.S. Cl.
CPC ...... *A61F 2/30724* (2013.01); *A61F 2/30965* (2013.01); *A61F 2/36* (2013.01); *A61F 2002/30672* (2013.01); *A61F 2002/30677* (2013.01); *A61F 2002/368* (2013.01); *A61F 2310/00353* (2013.01)

(58) Field of Classification Search
CPC ........ A61F 2/36; A61F 2/3607; A61F 2/3609; A61F 2/3662; A61F 2/30724; A61F 2002/3658; A61F 2002/3639
See application file for complete search history.

(56) References Cited

U.S. PATENT DOCUMENTS

| | | | | |
|---|---|---|---|---|
| 3,228,393 A | * | 1/1966 | Michele .................... | A61F 2/36 623/23.15 |
| 3,744,061 A | * | 7/1973 | Frost ......................... | A61F 2/32 623/22.11 |
| 5,746,771 A | * | 5/1998 | Clement, Jr. ...... | A61B 17/1659 623/23.22 |

(Continued)

FOREIGN PATENT DOCUMENTS

| | | | | |
|---|---|---|---|---|
| FR | 2760355 | | 9/1998 | |
| FR | 2935893 B1 | * | 12/2011 | ........... A61F 2/3662 |

OTHER PUBLICATIONS

International Search Report dated Mar. 30, 2017 for PCT/IB2016/057964 (3 pages).

*Primary Examiner* — Marcia L Watkins
(74) *Attorney, Agent, or Firm* — Tutunjian & Bitetto, P.C.

(57) ABSTRACT

Core for a spacer, including a main body that comprises a plurality of through openings, adapted to be secured in a corresponding residual bone bed of a previous implant; the main body being adapted to be covered with a layer (S) of a coating material or a material including acrylic bone cement added or that can be added with one or a plurality of pharmaceutical products or active and/or therapeutic substances.

19 Claims, 3 Drawing Sheets

(56) References Cited

U.S. PATENT DOCUMENTS

| | | | | |
|---|---|---|---|---|
| 5,755,811 A * | 5/1998 | Tanamal | ............... | A61F 2/367 |
| | | | | 623/23.35 |
| 6,508,840 B1 * | 1/2003 | Rockwood, Jr. | ......... | A61F 2/40 |
| | | | | 128/898 |
| 9,381,086 B2 * | 7/2016 | Ries | ..................... | A61F 2/36 |
| 2010/0042213 A1 | 2/2010 | Nebosky et al. | | |
| 2014/0288659 A1 | 9/2014 | Vogt | | |
| 2014/0350691 A1 * | 11/2014 | Linares | ............... | A61F 2/3609 |
| | | | | 623/22.45 |
| 2015/0018832 A1 | 1/2015 | Vogt | | |
| 2016/0235955 A1 * | 8/2016 | Magagnoli | ............ | A61M 37/00 |
| 2016/0287396 A1 * | 10/2016 | Huff | ..................... | A61F 2/3609 |

\* cited by examiner

FIG. 1

CORE FOR A SPACER

TECHNICAL FIELD OF THE INVENTION

The present invention relates to a core for a spacer.

More particularly, the present invention relates to a core for a spacer adapted for the two-phase treatment of arthroprosthesis infections, e.g. hip prostheses, humeral prostheses, knee prostheses, ankle prostheses, etcetera.

STATE OF THE PRIOR ART

Arthroprosthesis infections are among the most feared causes of arthroprosthesis failure.

With specific reference to the hip prostheses, such events occur rather constantly, with a percentage variable between 0.5% and 6% of the cases.

The percentage of negative events increases in the case of re-implants or in the presence of risk factors such as previous operation, local hematoma, existing infectious diseases, local or general bone pathologies, immune depression, etcetera.

One method for treating the infection, defined two-phase treatment, provides for a first step of removing the infected arthroprosthesis: indeed, the chance of success with only conservative antibiotic treatment is rather limited.

The second treatment step consists of the new re-implant of the arthroprosthesis, once the tissues of the patient have been rehabilitated with regard to the infection.

In order to be able to maintain the necessary space for the new re-implant of a prosthesis and, above all, for treating the infection, the same applicant has developed spacer devices for temporary use, also termed temporary spacers, which release pharmaceutical products and/or therapeutic products, such as antibiotics, and allow maintaining the articular mobility and anatomic size of the patient.

It was observed that one of the most decisive factors in determining the success of the aforesaid treatment is constituted by the possibility of being able to constantly release the pharmaceutical and/or therapeutic products for a time period as prolonged as possible, in a manner so as to have a release of such substances which affects all of the areas of the bone tissue to be treated.

Nevertheless, in order to be able to do this, the spacer device must remain in the human body for a certain time period, during which it must support the mechanical stresses and loads due to the movements made by the patient in the course of his/her activities.

SUMMARY OF THE INVENTION

The technical task of the present invention is to improve the state of the art.

In the scope of such technical task, one object of the present invention is to make a core for a spacer that allows prolonging the times of release of pharmaceutical and/or therapeutic products.

Another object of the present invention is to implement a core for a spacer that is light but at the same time optimal from the standpoint of the strength characteristics during use.

Another object of the present invention is to provide a core for a spacer that is simple and inexpensive to make.

Such task and such objects are all achieved by the core for a spacer according to the present application.

A further technical task of the present invention is to implement a method for making a spacer device that allows prolonging the times of release of pharmaceutical and/or therapeutic products.

Another object of the present invention is to implement a method for making a spacer device that is simple and inexpensive.

A further object of the present invention is to implement a method for making a spacer device that is easily adaptable to the needs of the surgeon who executes the operation.

Such task and such objects are all achieved by the method for making a spacer device comprising a core according to the invention according to the present application.

The core according to the invention comprises a stem, adapted (after having been further covered with a specific coating material) to be fixed in a corresponding residual bone bed of a previous implant, and a neck connectable to a further portion of the spacer insertable in a specific articular region of the patient; the stem and the neck are covered with a layer of a coating material comprising acrylic bone cement or they are adapted to be covered in such a manner so as to obtain the resulting spacer device.

According to the invention, the stem comprises a plurality of through openings containing said coating material, or containing a material comprising acrylic bone cement added with one or a plurality of pharmaceutical products or active and/or therapeutic substances.

In one embodiment of the invention, the same coating material comprises acrylic bone cement added with one or a plurality of pharmaceutical products or active and/or therapeutic substances.

In one embodiment of the invention, the product added to the acrylic bone cement is constituted by an antibiotic.

The present application refers to preferred and advantageous embodiments of the invention.

BRIEF DESCRIPTION OF THE DRAWINGS

These and further advantages will be better understood by every man skilled in the art from the following description and enclosed drawings, given as a non-limiting example, in which.

DETAILED DESCRIPTION OF THE INVENTION

Figure 1:
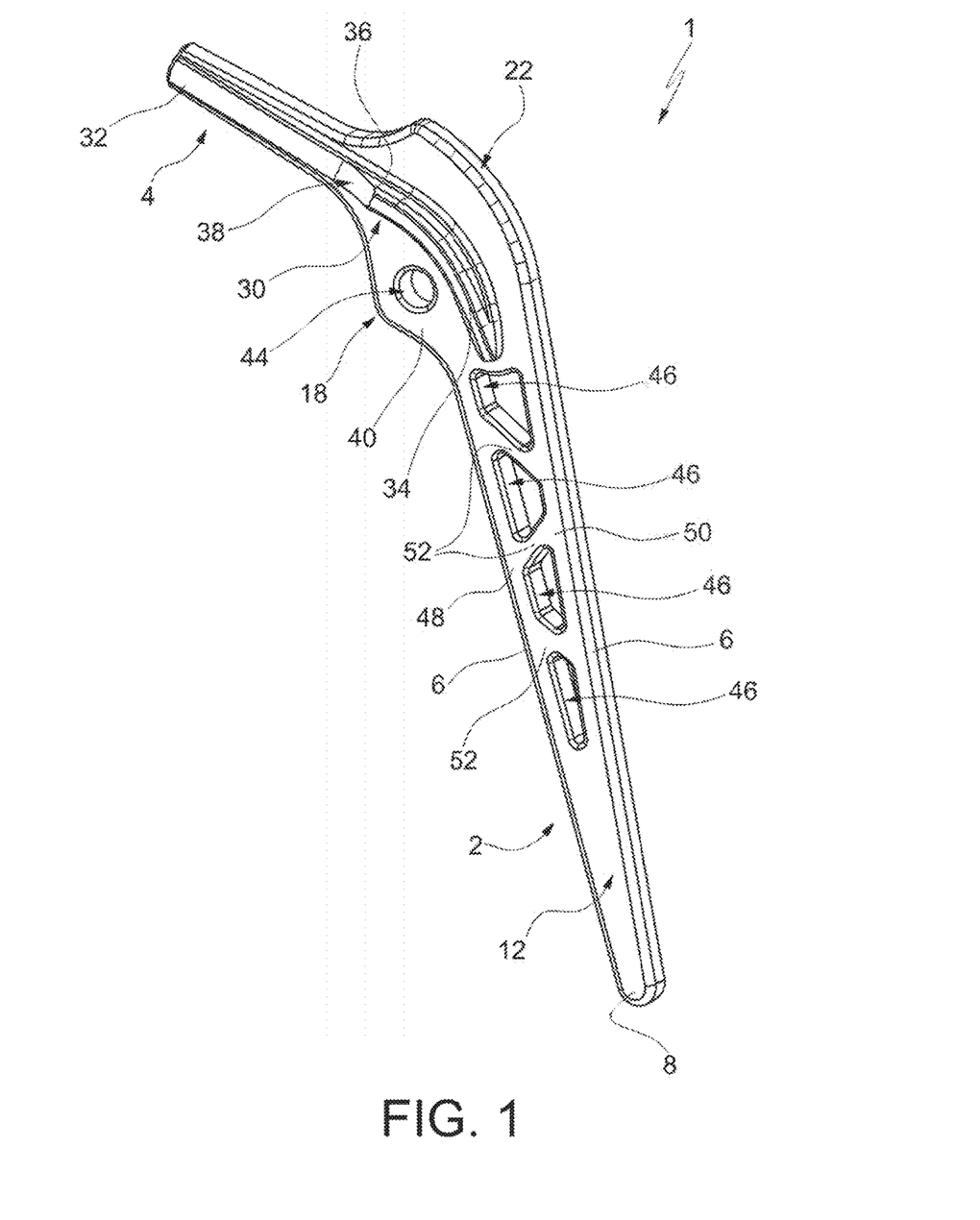
FIG. 1 is a perspective view of the core for a spacer according to the invention.

With reference to FIG. 1, reference number 1 overall indicates, only as an explicative and non-limiting example, a core for a spacer device adapted to be secured in a corresponding residual bone bed of a previous implant. In turn, as will be better described hereinbelow, the core is adapted to be secured in a corresponding residual bone bed of a previous implant.

The core 1 is an internal core; said internal core is adapted to be suitably covered for the obtainment of a spacer device.

The core 1 comprises a main body. In the version illustrated in the enclosed figures, such main body comprises a stem 2.

The main body or stem 2 is adapted to be secured, for example, in a corresponding residual bone bed of a previous implant. However, before it can be implanted, at least in one version of the invention, the main body or stem 2 is covered with a suitable material, as will be better clarified in the course of the present description.

In the illustrated version, the core 1 comprises a neck 4. The neck 4 is rigidly connected to the stem 2.

More particularly, and as better described hereinbelow, the main body or the core 1 is made of a single piece.

In the illustrated version, therefore, the neck 4 and the stem 2 are integral with each other.

The neck 4 can be adapted to be connected to a further portion of the spacer, not represented in the figures.

For example, in one embodiment of the invention, such further portion could be constituted by a spherical head, insertable in a specific articular region of the patient (e.g. a hip, a shoulder or still other regions).

In other embodiments of the invention, the aforesaid portion could be constituted by another component, with different shape and/or having a different destination.

Hereinbelow, the version of the invention illustrated in the figures will be described, as an example and without being considered a limitation of the present protective scope.

The stem 2 and the neck 4 both have substantially elongated shape, and different lengths (the stem 2 has length greater than the neck 4).

The respective longitudinal axes of the stem 2 and of the neck 4 define a certain angle between them.

For example, such angle is an obtuse angle that approximates the natural tilt existing between the body and the femur neck (in the case of hip prosthesis), or between the body and the neck of the humerus (in the case of humeral prosthesis).

The stem 2 or the main body has rectangular or substantially rectangular cross section, with the corners connected.

The lateral edges 6 of the stem 2 or of the main body are then suitably rounded, for anatomic reasons and in order to prevent injuries of the operator who handles the object, and also in order to facilitate the insertion of such component in the human body.

Figures 2, 3, 4:
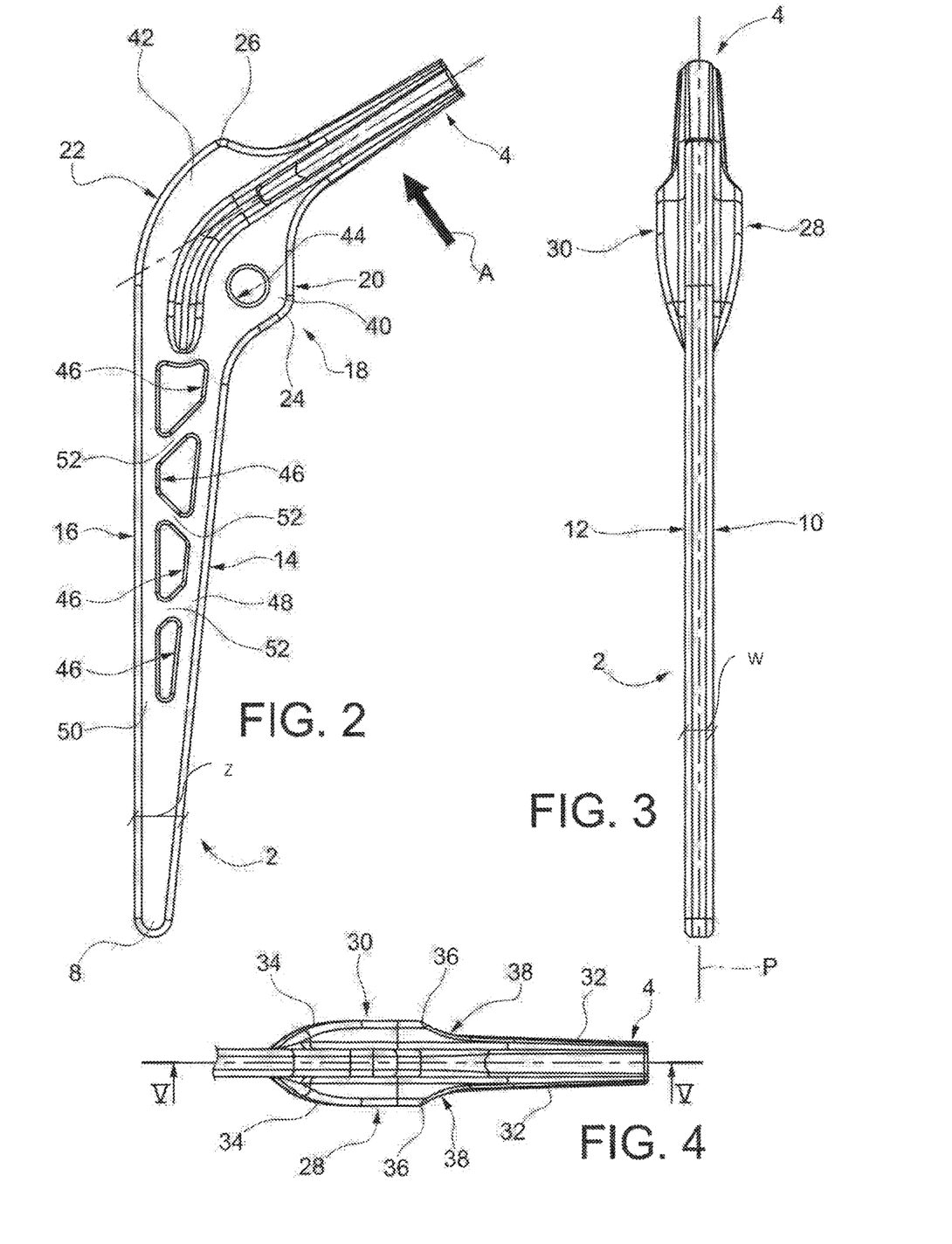
FIG. 2 is a front view of the core.
FIG. 3 is a side view of the core.
FIG. 4 is a particular view of the core along the direction indicated by the arrow A of FIG. 2.

The cross section of the stem 2 has substantially constant thickness W, where by thickness W of the cross section it is intended the size of the stem 2 itself detectable in the side view of FIG. 3 (in other words, the thickness W of the stem 2).

Analogously, the thickness of the main body can be substantially constant.

The width Z of the cross section of the stem 2 (by width Z of the section it being intended the size thereof detectable in the front view of FIG. 2) is instead progressively increasing, from the free end 8 of the stem 2 proceeding towards the neck 4.

In other words, the stem 2 or the main component comprises a first face 10 and a second face 12 parallel or plane-parallel (i.e. for example the stem 2 has constant thickness W when observed laterally, see FIG. 3). In one version of the invention, the first face 10 and a second face 12 are substantially parallel to each other, i.e. equidistant.

In addition, when observed frontally (FIG. 2), the main component or the stem 2 has a first side 14 and a second side 16 that are flat or substantially flat, and are not parallel to each other.

In other words, in one embodiment of the illustrated version, the first side 14 and the second side 16 form an acute angle with each other that has a vertex at the free end 8 of the stem 2, i.e. they converge towards the free end 8 itself.

The free end 8 of the stem 2 is connected with a specific radius, for the grounds set forth above.

A connector zone 18 can be provided between the stem 2 and the neck 4.

The connector zone 18 is delimited by two opposite lateral surfaces 20,22, respectively connected to the first side 14 and to the second side 16.

Such lateral surfaces 20,22, for a certain section and proceeding from the stem 2 towards the neck 4, progressively diverge, and simultaneously are curved by following the tilt variation in the passage from the stem 2 to the neck 4 themselves.

In a further subsequent section, the lateral surfaces 20,22 form respective kinds of cusps 24,26, at which they vary the tilt thereof and instead proceed by converging towards the neck 4.

The neck 4 (observed frontally as in FIG. 4) has transverse width greater than that of the stem 2.

The above-described section variations between the stem 2 and the neck 4 are obtained with suitable connections in order to eliminate sharp edges, and so as to reproduce the anatomic forms of the affected bone portions as accurately as possible.

The core 1 or the main body, observed laterally (FIG. 3), is symmetric with respect to a plane of symmetry P.

According to one aspect or variant of the invention, the core 1 comprises a first rib 28. The first rib 28 is provided on the first face 10.

In addition, the core 1 comprises a second rib 30. The second rib 30 is provided on the second face 12.

The second rib 30 can be identical to the first rib 28, and arranged symmetrically with respect to the latter, with respect to the plane P.

By frontally observing the core 1 (FIG. 3), each of the ribs 28,30 affects the neck 4 for the entire length thereof, substantially starting from the connector zone 18. Therefore, in such version, also the connector zone 18 is affected by the ribs 28,30.

Still frontally observing the core 1, each of the ribs 28,30 is curved, since it follows the tilt variation in the passage from the neck 4 to the stem 2.

According to another aspect of the invention, the cross section of each of the ribs 28,30 varies from one end to the other of the same.

More particularly, each of the ribs 28,30 has cross section with minimum surface area at the neck 4.

Each of the ribs 28,30 comprises a respective first section 32, which is extended along the neck 4.

The first section 32 has cross section with substantially constant (and minimum) surface area for a certain length, proceeding from the end of the neck 4.

Each of the ribs 28,30 also comprises a second section 34, connected to the respective first section 32 by means of a connector portion 36.

The second section 34 (observed frontally) is curved, and is extended through the connector zone 18; the second section 34 has cross section with constant (and maximum)

surface area for a certain length, and which then decreases proceeding towards the stem 2.

The cross section of the connector portion 36 varies, passing from the first section 32 to the second section 34, so as to define a concave surface 38.

The connector zone 18 between the stem 2 and the neck 4 in particular comprises a first portion 40 and a second portion 42.

The first portion 40 is the internal portion with reference to the angle defined by the stem 2 and by the neck 4, while the second portion 42 is the external portion with reference to the same angle.

According to one aspect of the invention, the first portion 40 comprises a through hole 44, whose functions will be better described hereinbelow.

According to another aspect of the invention, the core 1 comprises a plurality of through openings 46 made in the stem 2 or in the main body.

By through opening, it is intended an opening that traverses the entire thickness W or the entire width Z of the main body of the core 1.

For example, in at least one version of the invention, the openings 46 are through in the sense that they have a substantially rectilinear progression starting from the first face 10 up to the second face 12 of the main body of the core 1. Therefore, the through openings 46 affect both the first face 10 and the second face 12 of the main body of the core 1.

In a further version, possibly alternative, the openings 46 are through in the sense that they have a substantially rectilinear progression starting from the first side 14 up to the second side 16 of the main body of the core 1. Therefore, the through openings 46 affect both the first side 14 and the second side 16 of the main body of the core 1.

The through openings 46 are aligned, or substantially aligned, along the axis of the stem 2 or along an axis of the main body of the core 1 or along a main axis or main longitudinal axis of the main body of the core 1.

In one version of the invention, the through openings 46 have decreasing size when moving from the connector zone 18 towards the free end 8 of the stem 2 itself.

In this manner, the strong section of the stem 2 is uniform at the portions where the through openings 46 are present.

More in detail, the through openings 46 are defined between two continuous and substantially rectilinear lateral portions 48,50 of the stem 2 or of the main body, which have or can have the same cross section.

In the embodiment illustrated in the figures, the stem 2 comprises four through openings 46.

The through openings 46 are separated from each other by transverse elements 52, which connect the two lateral portions 48,50.

In the illustrated version, the transverse elements 52 are tilted with respect to the longitudinal axis of the stem 2 by respective predetermined angles.

In a further version, the transverse elements 52, possibly rectilinear, can also have other tilts, without departing from the protective scope of the present invention.

In particular, three transverse elements 52 are provided in the illustrated version, which separate the four through openings 46 from each other, and which have tilts alternately opposite each other with respect to the longitudinal axis of the stem 2.

In this manner, the through openings 46 confer a substantially reticular structure to the stem 2.

In other embodiments of the invention, the stem 2 in particular or the main body of the core 1 could have different shape from that represented in FIGS. 1-5.

For example, the stem 2 or the main body could comprise a different number of through openings 46, and/or through openings 46 that are differently shaped and/or distributed.

Figure 5:
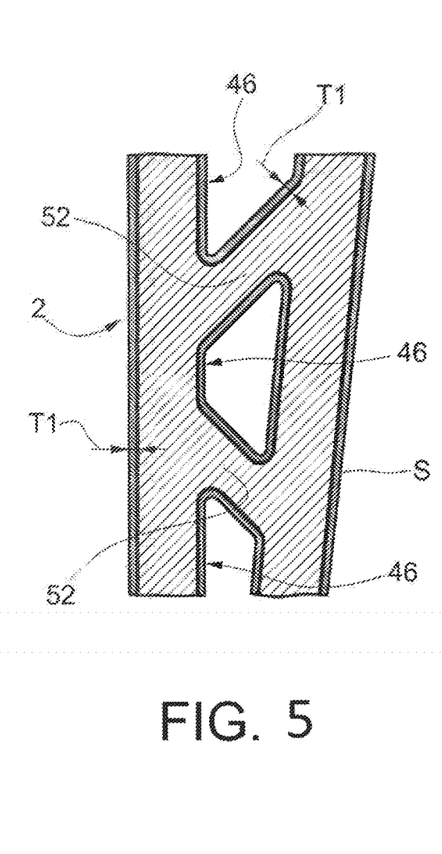
FIG. 5 is a detailed section of the core executed along the plane V-V of FIG. 4.

According to another aspect of the invention, the core 1 comprises a layer S of coating material (see FIG. 5).

In particular, the main body and/or the through openings 46 comprise a layer S of coating material.

In one version of the invention, before being implanted in the human body, the core 1 is covered (at least partially or, preferably, along the entire at least external surface thereof) with the coating material.

In one version of the invention, the coating material is hardened, before the core 1 is adapted to be implanted in the human body.

In a still further version, the core 1 is preformed by the manufacturer already covered (at least partially or, preferably, along the entire at least external surface thereof) with the coating material.

In one embodiment of the invention, the layer S can have uniform or substantially uniform thickness T1 over the entire surface of the core 1.

The thickness of the layer S can for example be comprised between 0.1 mm and 0.5 mm.

More preferably the layer S has thickness comprised between 0.1 mm and 0.2 mm.

Still more preferably the thickness of the layer S is 0.1 mm, or 0.2 mm.

In one embodiment of the invention, the coating material comprises, or is constituted by, acrylic bone cement.

The coating material can be added with at least one pharmaceutical product, or an active and/or therapeutic substance.

In another embodiment of the invention, the coating material comprises acrylic bone cement added with a pharmaceutical product, or an active and/or therapeutic substance, or a plurality of pharmaceutical products, active and/or therapeutic substances.

The pharmaceutical product, or the active and/or therapeutic substance, or the pharmaceutical products, active and/or therapeutic substances, can comprise antibiotics, antiseptics, antimycotics, chemotherapeutic agents, for example gentamicin, vancomycin, etcetera, or other active substances.

In one embodiment of the invention of particular practical interest for the treatment of arthroprosthesis infections, the layer S of coating material can comprise acrylic bone cement added with an antibiotic.

According to the invention, the through openings 46 mainly have material accumulation function.

More in detail, the material accumulated in the through openings 46 can be the same coating material with which the layer S is made; this solution is particularly interesting in the case in which the coating material comprises acrylic bone cement added or that can be added with an antibiotic.

Then, the accumulation of material in the through openings 46 can be carried out during the obtainment of the core 1 and during the application of the coating layer S.

Therefore, in one such version, the core 1 and the layer S of coating material are preformed by the manufacturer. In such case, they are ready for the implant in the human body and the surgeon can, if necessary, add a pharmaceutical product, or an active and/or therapeutic substance. In this case, the coating material is hardened or solid, before the core 1 is adapted to be implanted in the human body.

According to another aspect of the invention, and possibly as an alternative to the preceding solution, the through openings 46 can also be used for accumulating material not during the making of the core 1, but instead during the execution of the implant of the spacer device.

In other words, during the execution of the implant, the cement can be accumulated inside the aforesaid through openings 46, in order to improve the mechanical strength and hold characteristics of the implant itself.

In addition, in such a manner, the material accumulated inside the through openings 46 can act as a tank for a quantity of the at least one pharmaceutical product, or active and/or therapeutic substance.

Indeed, in the latter case, and upon completed implant, the material that traverses the thickness of the stem 2 or of the main body, and/or which is accumulated inside the cavities 46, once solidified, allows making particularly effective mechanical constraints for securing inside the bone bed. Analogously, such material strengthens the structure of the core 1.

In a still further version, the core 1 can comprise a layer S, S1 of coating material preformed by the manufacturer. Such layer S, S1 at least partially covers the external surface of the main body of the core 1 and can cover or not the internal surface (or through surface) of the through openings 46. In addition, the latter, during the step of implant of the core 1 (or of the relative spacer device), can be further filled with coating material, equal to or different from that of the layer S.

The abovementioned through hole 44 can have the function of lightening the core 1.

In addition, also the through hole 44 can be used, during the implant in the bone bed, to allow the passage of the securing cement or of the coating material that, once solidified, allows to make particularly effective mechanical constraints inside the bone bed itself.

In one embodiment of the invention, the core 1 can be made of a biocompatible metal alloy, such as for example a titanium alloy, or of another suitable biocompatible metal alloy.

More in detail, in one embodiment of the invention of particular practical interest, the core 1 can be made of a single piece of a biocompatible metal alloy, such as for example a titanium alloy, or of another suitable biocompatible metal alloy.

Figure 6:
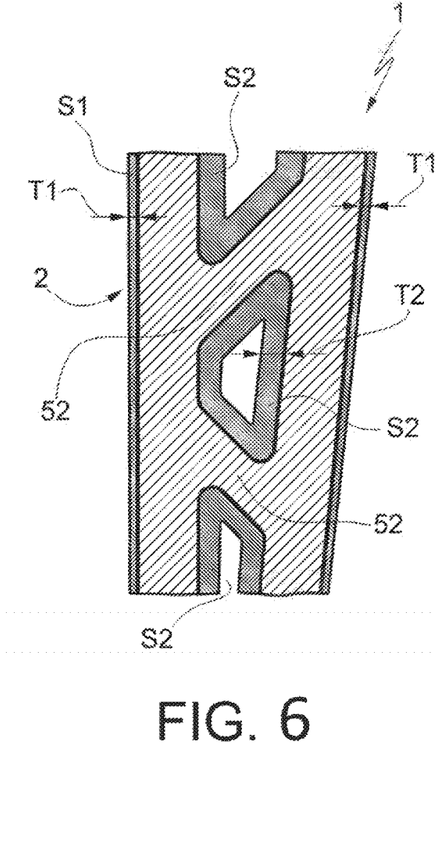
FIG. 6 is a detailed section of the core executed along the plane V-V of FIG. 4, according to another embodiment of the invention.

Another embodiment of the invention is illustrated in the detailed section of FIG. 6.

In this embodiment, the core 1 has the same geometric form of the embodiment according to FIGS. 1-5 or in any case described above.

Also in this embodiment, the core 1 comprises a layer S1 of coating material (having the above-described characteristics) with uniform or substantially uniform thickness T1 over the entire surface of the core 1 itself, except for the internal surfaces of the through openings 46.

In addition, in this embodiment, and according to a further aspect of the invention, especially at the internal surfaces of the through openings 46 of the stem 2, a further layer S2 of coating material is provided having a thickness T2 greater than the thickness T1 of the layer S1.

In other words, the through openings 46—as mentioned above—can be used for accumulating a greater quantity of material with respect to the remaining portions of the core 1.

This solution becomes particularly interesting in the case in which the coating material comprises a pharmaceutical product, or an active and/or therapeutic substance, such as an antibiotic.

In fact, since the release of the product added into the acrylic cement, such as for example an antibiotic, occurs in a very gradual manner over time, the possibility to be able to accumulate it inside the through openings 46 in greater quantity allows considerably extending the release times for the product in question.

Alternatively, the core 1 can be entirely covered with a layer S1 of coating material comprising acrylic bone cement lacking additives, while the internal surfaces of the through openings 46 can be selectively covered with a further layer S2 of material comprising acrylic bone cement added with at least one pharmaceutical product or an active and/or therapeutic substance.

Additionally, a possible second pharmaceutical product or an active and/or therapeutic substance can be added at at least one zone or through opening 46 of the core 1, when the coating material S, S1 or S2 already comprises a first pharmaceutical product or an active and/or therapeutic substance.

Figure 7:
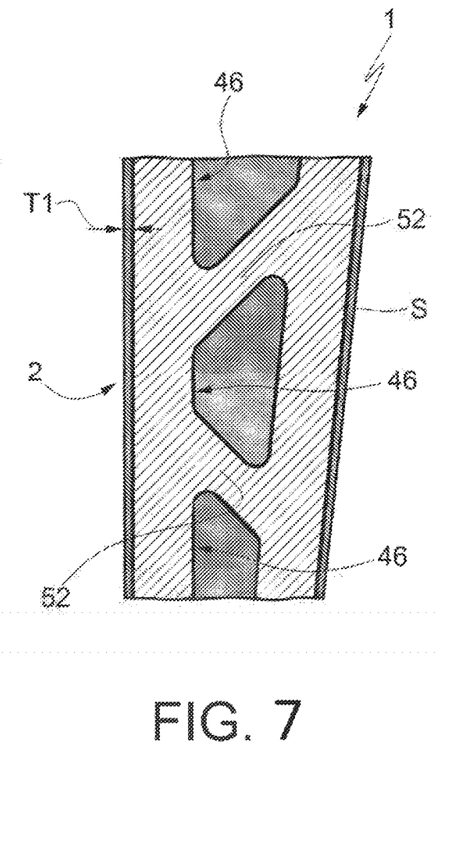
FIG. 7 is a detailed section of the core executed along the plane V-V of FIG. 4, according to still another embodiment of the invention.

Another embodiment of the invention is illustrated in the detailed section of FIG. 7.

In this embodiment, the core 1 has the same geometric shape as the embodiment according to FIGS. 1-5 or in any case as that described above.

Also in this embodiment, the core 1 comprises a layer S of coating material (having the above-described characteristics) with uniform or substantially uniform thickness T1 over the entire surface of the core 1 itself.

In addition, in this embodiment, and according to a further aspect of the present invention, the through openings 46 of the stem 2 are filled with a material comprising acrylic bone cement added with a pharmaceutical product or an active and/or therapeutic substance, such as for example an antibiotic (which can also be the same material used for making the coating layer S).

In this case, therefore, the through openings 46 are occluded.

If the through openings 46 are completely occluded, the stem 2 or the main body of the core 1 has a solid form and/or a smooth external surface, or substantially smooth external surface, i.e. in other words lacking discontinuities.

In this embodiment, the effect of extending the release times for the pharmaceutical product, or for the active and/or therapeutic substance, such as for example an antibiotic, is further emphasized, a considerable quantity of such product/substance being accumulated in the through openings 46.

At the same time, the through openings 46 are not used during the execution of the implant for allowing the passage of cement for securing to the bone bed.

Alternatively, if the acrylic bone cement is applied to the core 1 shortly before the implant of the core, it can also simultaneously act as cement for securing to the bone bed.

It is thus seen that the invention attains the proposed objects.

The core 1 according to the invention allows accumulating a greater quantity of material comprising a pharmaceutical product or an active and/or therapeutic substance with respect to the currently existing solutions.

This signifies that the spacer comprising the core 1 can release the product added to the acrylic bone cement for a greater time period with respect to the known solutions.

In addition, since the bone cement can be applied to the core 1 before the implant thereof, the surgeon can select, on the basis of the anatomic and therapeutic needs of the patient, to apply a greater or lesser quantity of bone cement and/or to add to the same one or more pharmaceutical substances, possibly with respect to those already present in the core 1, if actually present.

These results are obtained with a core solution that is very light but simultaneously strong, that is simple and inexpensive to produce.

In addition, given that the material added with a pharmaceutical product or an active and/or therapeutic substance is accumulated in considerable quantities inside the through openings 46, it may also be possible to avoid covering the entire external surface of the core 1 with a coating material added with the aforesaid product.

In one version of the invention, a spacer device is provided comprising the core 1.

In a still further version, the spacer device consists of the core 1 and the material that determines the layer S, S1, S2 of acrylic bone cement.

The acrylic bone cement, at least in one version of the invention, is a bone cement based on polymethylmethacrylate.

In a still further version, the invention consists of the method for making a spacer device comprising the steps of providing a core 1 equipped with a main body and with at least one opening 46 and of applying the material constituting the layer S, S1, S2 to the core 1 or to the main body or to at least part thereof.

In addition, a step is provided for immersing the core 1 in a solution containing the acrylic bone cement in a manner so as to apply such material to the surfaces of the core 1, thus determining the formation of the layers S, S1, S2.

Possibly, a further step can be provided for immersing or applying to at least some zones of the core 1 the previously applied material or a different material, in order to create a further layer thereof.

A further step of the method provides for solidifying such material.

The present invention was described according to preferred embodiments, but equivalent variants can be conceived without departing from the protective scope offered by the following claims.

The invention claimed is:

1. A core for a spacer device suitable to be secured in a corresponding residual bone bed of a previous implant, wherein said core comprises:
    a main body, wherein said main body comprises a plurality of through openings,
        wherein said main body is covered with a layer (S, S1) of a coating material and said through openings are covered with said coating material, said coating material comprising at least one of a pharmaceutical product, active, or therapeutic substances,
        wherein said main body comprises a stem and a neck defining a longitudinal axis, said neck being connectable to a further portion of the spacer insertable in a specific articular region of a patient,
    wherein said core comprises a first rib and a second rib which are symmetrical and opposite with respect to one another, and which first and second ribs extend continuously along said neck for its entire length and also extend continuously from the neck along a connecting zone between said neck and said stem, wherein each of the first and the second ribs comprises a first section connected to a second section, wherein each of the second sections of each rib are curved away from the longitudinal axis toward a distal end of the stem.

2. The core according to claim 1, wherein said coating material comprises acrylic bone cement added with one or a plurality of pharmaceutical products, active and/or therapeutic substances.

3. The core according to claim 1, wherein said layer (S) has a uniform thickness (T1) over the entire surface of said core.

4. The core according to claim 1, wherein said core is an inner core, covered with the layer (S, S1) of the coating material to obtain the spacer device.

5. The core according to claim 1, wherein said main body is made in a single piece of a biocompatible metal alloy.

6. The core according to claim 1, wherein said through openings are aligned, along a longitudinal axis of said stem.

7. The core according to claim 1, wherein said main body comprises a first side and second side, wherein said first side and second side are flat, arranged to provide between each other an acute angle that has a vertex at a free end of said main body, said through openings having dimensions progressively decreasing toward said free end.

8. The core according to claim 1, wherein said through openings are delimited between two continuous and rectilinear lateral portions of said main body, wherein said two lateral portions have the same cross section.

9. The core according to claim 8, wherein said through openings are separated from one another by transverse elements that connect said lateral portions.

10. The core according to claim 9, wherein said transverse elements are inclined with respect to a longitudinal axis of said stem by respective predetermined angles, so as to impart to said main body a reticular or trabecular structure and/or wherein said through openings define in said main body a substantially reticular or trabecular structure.

11. The core according to claim 1, wherein said layer (S, S1) of coating material has a thickness comprised between 0.1 mm and 0.5 mm.

12. The core according to claim 11, comprising a further layer of coating material or of a material comprising acrylic bone cement added with the at least one pharmaceutical product, active or therapeutic substances, having a thickness (T2) greater than a thickness), provided at internal surfaces of said through openings.

13. The core according to claim 11, wherein the thickness of the layer (S, S1) of coating material is between 0.1 mm and 0.2 mm.

14. The core according to claim 1, wherein said through openings are filled with said coating material or with a material comprising acrylic bone cement added with the at least one pharmaceutical product, active or therapeutic substances, so as to become occluded.

15. The core according to claim 1, wherein said at least one pharmaceutical product, active or therapeutic substances comprise antibiotics, antiseptics, antimycotics, or chemotherapeutic agents.

16. A spacer device comprising a core according to claim 1.

17. A method for a realization of a spacer device suitable to be secured in a corresponding residual bone bed of a previous implant, comprising the following steps:
    providing an inner core comprising a main body, said main body being provided with a plurality of through openings, said main body comprising a stem and a neck, said neck being connectable to a further portion of the spacer insertable in a specific articular region of a patient, wherein said core comprises a first rib and a second rib which are symmetrical and opposite with respect to one another, and which engage said neck continuously along its entire length and also extend continuously from the neck along a connecting zone of said neck to said stem, wherein each of the first and the second ribs comprises a first section connected to a second section, wherein each of the second sections of each rib are curved away from a longitudinal axis of the neck towards a distal end of the stem, coating or applying to said core at least one layer (S; S1) of a coating material, so that at least part of an external surface of said core and/or said plurality of through openings is/are covered and/or contains/contain said coating material, comprising at least one pharmaceutical product, active or therapeutic substances.

18. The method according to claim 17, further comprising coating or applying on at least part of said core including on the plurality of through openings at least one layer (S2) of a coating material.

19. The method according to claim 17, wherein said step of coating or applying comprises immersing said core or a part thereof into said coating material.

* * * * *